US00PP08472P

United States Patent [19]

Gwaltney

[11] Patent Number: Plant 8,472

[45] Date of Patent: Nov. 23, 1993

[54] ABELIA×GRANDIFLORA VARIETY NAMED 'CONTI'

[75] Inventor: James T. Gwaltney, Theodore, Ala.

[73] Assignee: Flowerwood Nursery Inc., Mobile, Ala.

[21] Appl. No.: 877,948

[22] Filed: May 1, 1992

[51] Int. Cl.[5] ..... A01H 5/00
[52] U.S. Cl. ..... Plt./54.1
[58] Field of Search ..... Plt./54.1

[56] References Cited

U.S. PATENT DOCUMENTS

P.P. 1,431 11/1955 Abbott ..... Plt. 54.1
P.P. 7,634 8/1991 Frazer ..... Plt. 88.1

*Primary Examiner*—James R. Feyrer
*Assistant Examiner*—Erich E. Veitenheimer

[57] ABSTRACT

The new plant is readily distinguishable from other *Abelai×grandiflora* as the Abelia described herein does not have the same characteristics as other Abelias in growth habit, or foliage color as described in horticultural literature.

2 Drawing Sheets

BACKGROUND OF THE INVENTION

This new variety of *Abelia×grandiflora* was found as a sport of *Abelia×grandiflora* 'Sherwoodi' maintained in the Flowerwood Nursery at Dauphin Island Parkway, Mobile, Ala. The sport was found in August, 1987. Asexual propagation of the new plant by cuttings has been under Mr. Gwaltney's direction at the same location. The increased number of plants were evaluated and demonstrated stability of the new characteristics from generation to generation.

SUMMARY OF THE INVENTION

The following are the most outstanding and distinguishing characteristics of this new cultivar when grown under normal horticultural practices in Mobile, Ala.

1. Ground cover in nature
2. The variegation of foliage is unique and beautiful. The effects of grey-green with cream variegated foliage is similar to other popular landscape shrubs and grasses with different growth habit. Those other species are *Liriope muscari* Variegata and *Ligustrum sinensis* Variegated.
3. New growth terminal, winter foliage and stems are pronounced with purple pigmentation.
4. Easy to root from cuttings collected any time of the year.
5. Fast growth rate under normal fertilization and moisture conditions.
6. Hardy to Zone 6
7. Drought tolerant
8. Relatively pest resistant

DESCRIPTION OF THE DRAWINGS

This new variety of *Abelia×grandiflora* is illustrated by the accompanying photographic prints in which.

Figure 1:
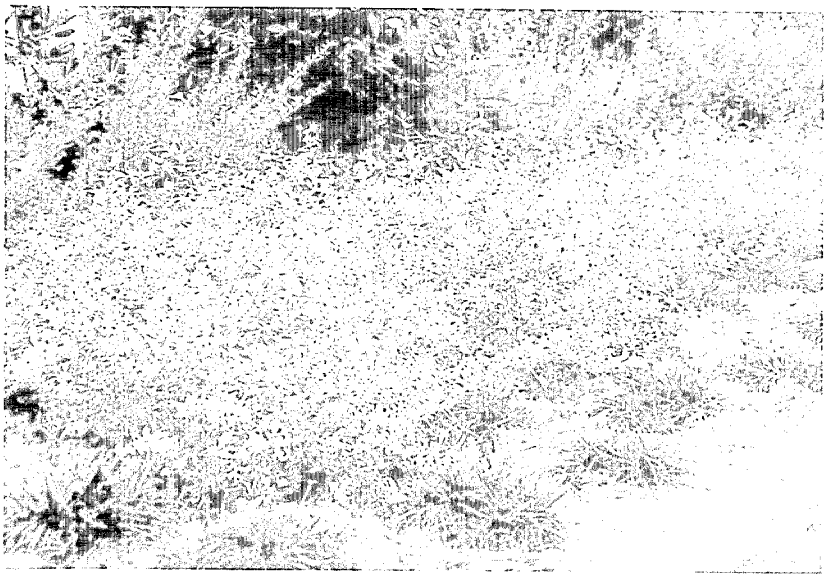
FIG. 1 discloses the prostrate or spreading nature of the new variety.
Figure 2:
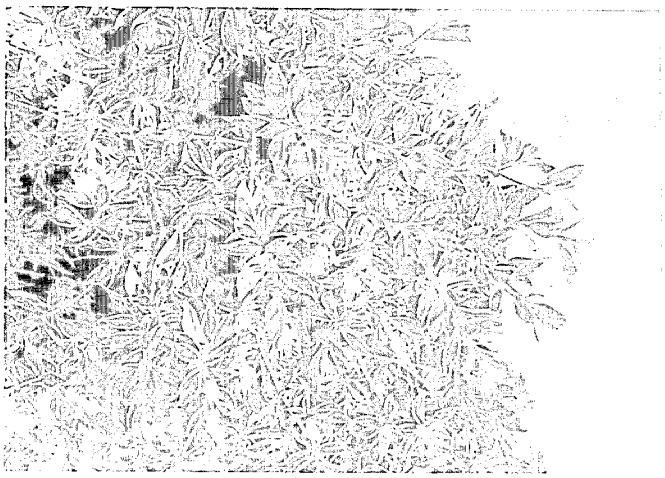
FIG. 2 discloses the unusual variegation of foliage and prominence of purple pigmentation of stem and petioles.
Figure 3:
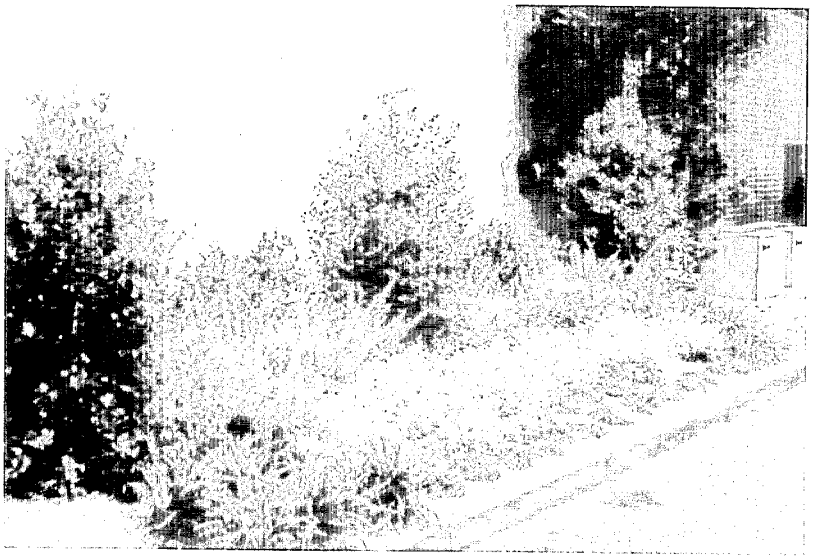
FIG. 3 shows the effective use and nature of use of the new variety in an established landscape planting.
Figure 4:
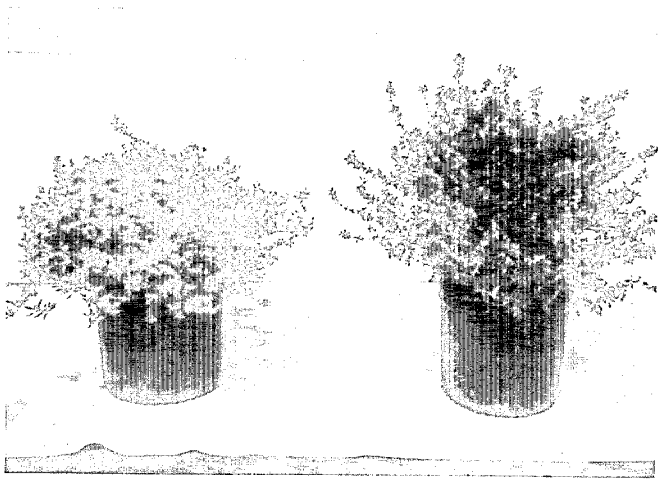
FIG. 4 is a side-by-side photograph with the parent variety 'Sherwoodi', which shows the densely branched and spreading habit of the new variety.

The colors shown are photographically as nearly true as is reasonably possible to obtain by conventional photographic procedures.

BOTANICAL DESCRIPTION OF THE PLANT

The following is a detailed description of the new variety of Abelia based on my observations made of plants grown in wholesale commercial production practices, in greenhouses, and established landscape plantings in Mobile, Ala.

DISTINCTIVE CHARACTERISTICS:

| Characteristic | 'Conti' | 'Sherwood' | 'Prostrata' |
|---|---|---|---|
| Height | 45–60 cm | 60–90 cm | 45–60 cm |
| Width | 120–150 cm | 120–150 cm | 120–150 cm |
| Leaf-width | 1.4 cm | 1.2 cm | 1.2 cm |
| Leaf-length | 2.3 cm | 2.3 cm | 2.4 cm |
| Stem | purple | pink | green |
| Flower | white | white | white |
| Foliage | grey-green cream yellow variegation | green | green |

The plant from which all of the above varieties originated has the botanical name Caprifoliaceae *Abelia×grandiflora*, Rehd. of the order Rubiaceae. This plant was produced from the cross *A. chinensis×A. uniflora*. The author of the species name Grandiflora is Alfred Rehder (1863–1949). From the plant *Abelia×grandiflora* came the variety 'Sherwoodi' and it was from this plant, *Abelia×grandiflora* 'Sherwoodi' that I found the new plant. This new variety will be sold under the trademark name Confetti. It will be listed *Abelia×grandiflora* Confetti TM 'Conti'.

Classification:

*Botanic.*—*Abelia×grandiflora* 'Conti'.

Form: Spreading. Although both plants are densely branched, the spreading habit is more pronounced in the new variety than in the parent variety *Abelia*×*grandiflora* 'Sherwoodi'.

*Height.*—22½ feet.

*Width.*—4–5 feet.

Growth: Low-growing, spreading, and prostrate. Can be fast growing under normal fertilization and moisture conditions.

Leaves: Opposite, simple, ovate, attenuate at the base, acute ½" to ⅞" long. Slightly serrate, shining above, nearly glabrous. The plant is semi-evergreen. In 1990, the date of initial spring growth was March 27, in Mobile, Ala. It had been a mild winter and the plants were almost completely evergreen. The following fall and winter was cold and approximately ⅓ of the foliage was shed during the winter starting Jan. 5, 1991.

Stems: Have a pronounced purple pigmentation during the winter. Young stems are pubescent, older stems are exfoliating and split to expose light inner bark. The plant is densely branched like Abelia 'Sherwood' but even more so than *Abelia*×*grandiflora*.

Flowers: Flowering more or less continuously from June to November. Flowers in terminals, loose panicles, white, bell-shaped, ½" long, ⅜" to ½" wide. There are 2 to 5 sepals per flower and they are from ⅜" to ½" long and are not persistent. There is always only one pistil. The stigma is white. There are either two or three stamens. The filaments and anther are white. Flowering is usually profuse on the new growth of the season. There are 2 to 3 flowers together in leafy panicles at the end of lateral branches. There is only a slight fragrance. There can be several hundred flowers per plant. In 1992, the blooming period began June 8, in Mobile, Ala. and ended when we had a frost on November 23. The blooming period is basically identical to *Abelia*×*grandiflora* and *Abelia*×*grandiflora* 'Sherwoodi'.

Fruit: None.

Color: The colors are described according to the nearest colors of The Royal Horticultural Society Color Chart. The leaves are variegated and contain three primary colors, a creme yellow color (greyed yellow group 160c), which generally extends inwardly from the margins of the leaves, a deep green color (yellow green group 147A), which usually is expressed in the central portion of the leaves, covering more or less 70% of the total leaf surface area, and a combination of the two (greyed green group 194B), where one or more layers of cells of yellow overlay a layer of green cells. This laminating effect may look several layers deep and result in two or more intermediate colors of different shades. The two colors, greyed yellow group 160C and greyed green group 194B, each cover approximately 15% of the total leaf surface area. This variegation pattern varies from leaf to leaf and is probably derived from two or more genetically distinct histogenic regions of the leaf forming meristem and is thought to represent a periclinal type of chimera. Differences in chlorophyll content in regions of the leaf result in different colorations. The immature stems are noticeably pigmented and are purpler red group 60A. The mature stem is greyed purple group 183A. The flowers are white. The sepals are red purple group 64D. The immature foliage in the winter is red purple group 64D.

Culture: Grows well in a wide range of conditions. Tolerates sun or shade, any reasonable soil moist to fairly dry. Responds well to fertility.

Pests: None serious.

I claim:

1. A new and unique variety of *Abelia*×*grandiflora* named *Abelia*×*grandiflora* 'Conti' as herein shown and described, is characterized by its very spreading growth habit, its unique creamy variegation of foliage and winter coloration. The dense, compact, spreading growth habit will fill numerous landscape needs for ground covering, variegation coloration, drought tolerance, groupings and mass plantings, requiring less maintenance, especially pruning, than other species, and freedom from disease and insects with a wide soil tolerance.

* * * * *